(12) United States Patent
Manley et al.

(10) Patent No.: US 6,256,847 B1
(45) Date of Patent: Jul. 10, 2001

(54) STRAP FASTENER

(75) Inventors: Norman G. Manley, Leander; Brian M. Cox, Cedar Park, both of TX (US)

(73) Assignee: 3M Innovative Properties Company, Saint Paul, MN (US)

(*) Notice: Subject to any disclaimer, the term of this patent is extended or adjusted under 35 U.S.C. 154(b) by 0 days.

(21) Appl. No.: 09/316,156

(22) Filed: May 21, 1999

Related U.S. Application Data (63) Continuation-in-part of application No. 08/854,512, filed on May 12, 1997, now abandoned, which is a continuation-in-part of application No. 08/670,862, filed on Jun. 28, 1996, now abandoned.

(51) Int. Cl.[7] .................................................. A44B 17/00
(52) U.S. Cl. ............................................ 24/582; 24/168 B
(58) Field of Search .............................. 24/587, 580–584, 24/168 B, 30.5 P, 20 EE, 575, 577, 265 WS, 685; D8/394; 63/1.13, 3.2; 224/164, 165, 176; 368/281, 282; 40/633

(56) References Cited

U.S. PATENT DOCUMENTS

| | | |
|---|---|---|
| 3,147,522 | 9/1964 | Schumm . |
| 3,263,292 * | 8/1966 | Fekete . |
| 3,514,815 * | 6/1970 | Evans . |
| 3,518,727 * | 7/1970 | Eberle et al. . |
| 3,857,397 | 12/1974 | Brosseau . |
| 4,178,751 | 12/1979 | Liautaud . |
| 4,581,792 * | 4/1986 | Spier . |
| 4,677,521 | 6/1987 | Frazier . |
| 4,698,724 | 10/1987 | Burvee . |
| 4,872,242 * | 10/1989 | Allan . |
| 4,907,321 * | 3/1990 | Williams . |
| 4,941,236 | 7/1990 | Sherman et al. . |
| 4,944,072 * | 7/1990 | Robson . |
| 5,018,044 | 5/1991 | Weiss . |
| 5,057,965 | 10/1991 | Wilson . |
| 5,184,274 | 2/1993 | Weiss . |
| 5,339,499 | 8/1994 | Kennedy et al. . |
| 5,555,608 * | 9/1996 | Allan . |
| 5,878,468 * | 3/1999 | Tomic et al. . |

FOREIGN PATENT DOCUMENTS

| | | |
|---|---|---|
| 85 13 373 | 9/1986 | (DE) . |
| 2 141 358 | 1/1973 | (FR) . |
| 1 003 889 | 3/1998 | (NL) . |
| 186725 | 7/1992 | (TW) . |
| 264159 | 11/1995 | (TW) . |
| 273675 | 4/1996 | (TW) . |
| WO 98/00196 | 1/1998 | (WO) . |

* cited by examiner

Primary Examiner—James R. Brittain
(74) Attorney, Agent, or Firm—Charles D. Levine; Melanie Gover (57) ABSTRACT

A reclosable fastener includes an insert element and a retention element. The retention element has a plurality of discrete, spaced projections extending generally orthogonally from at least one side edge of one of the opposing surfaces. At least one of the projections has a free end that includes a hook portion extending generally orthogonally from the projection toward the central longitudinal axis. The fastener operates in first and second conditions. In the first condition the fastener is open and the insert element is disengaged from the retention element, and in the second condition the fastener is closed and the insert element engages the retention element. In moving from the first condition to the second condition the insert element engages the retention element by overlaying onto the retention element and being pressed into place. In moving from the second condition to the first condition the insert element disengages from the retention element by peeling from the retention element.

8 Claims, 9 Drawing Sheets

STRAP FASTENER

This is a continuation-in-part of application U.S. application Ser. No. 08/854,512 filed May 12, 1997, now abandoned, which is a continuation-in-part of application U.S. application Ser. No. 08/670,862, filed Jun. 28, 1996, now abandoned.

FIELD OF THE INVENTION

The present invention relates to fasteners and to devices for preventing electrostatic discharge. More particularly, the present invention relates to a fastener which can be polymeric.

BACKGROUND OF THE INVENTION

Electrostatic discharge, as well as the mere presence of a static electric field, can be extremely detrimental to sensitive electronic (solid-state) parts. Modern semiconductors and integrated circuits may be degraded or destroyed by such static buildup. One common tool used to control static discharge and buildup is a conductive grounding tether which is designed to drain away excess electrostatic charge. A general discussion of such devices can be found in U.S. Pat. Nos. 4,677,521, 5,018,044, and 5,184,274.

The wristbands and tethers disclosed in these patents have many parts which add to the cost of the devices. While those devices have features which make them advantageous for particular uses, they are relatively expensive when considered for the most basic task of safe and effective grounding. Less expensive and simpler bands have been designed, such as those shown in U.S. Pat. Nos. 3,857,397 and 4,698,724, but those designs suffer from certain inherent limitations. For example, both of these designs are unitary wristband/tethers, meaning that if the tether portion of the device breaks, the wristband becomes useless, or vice-versa, and also meaning that if the user desires to walk away from his or her workstation he or she must completely take off the wristband, or must allow the tether portion to dangle, in contrast with the designs that allow the tether to be detachably connected to the wristband. Both of these designs are also ill-suited for use in a dual conductor system (such as that shown in the '044 patent). Finally, the means for adjusting the effective size of the wristband must be applied separately to the band, such as the hook-and-loop fastening strips in the '397 patent, or the adhesive layer in the '724 patent This separate application step increases processing cost, but it is critical that the device achieve a proper exact adjustment since it must have good contact with the skin to be sufficiently conductive, and yet not be so tight to constrict circulation or otherwise be uncomfortable.

Alternatives to the hook and loop fastening described in the '397 patent require pressing together overlapping portions of a strap to establish interlocking contact to secure the strap in a looped configuration of desired dimensions. For example, U.S. Pat. Nos. 3,514,815, 3,518,727, and 4,872,242 provide elongated, flexible straps with means on their upper and lower surfaces for connection between surfaces. When formed into a loop, the straps are positioned with teeth on one surface adjacent to valleys on the opposite surface. The teeth and valleys will nest together, under suitable pressure, so that interlocking connection between teeth and valleys occurs. Upon wrapping one of the disclosed flexible straps around, for example, a cable bundle, the teeth and valleys provide interlocking means capable of self-engagement along a length where the strap overlaps itself.

U.S. Pat. Nos. 4,178,751 and 4,941,236 disclose interlocking structures for securing straps, associated with watches, around the wearer's wrist. The '236 patent discloses an interlocking means in the form of a clasp for a watch band. In this case the free end portions of the band include magnetic segments. End portions may be secured together under the influence of the magnetic force. The strap ends have surfaces contacting one another where they overlap with mutually nesting, uniformly spaced interlocking teeth; the magnetic segments provide a holding force resisting separation of the end portions while the nested teeth prevent sliding disengagement between the ends. In the '751 patent, an injection-molded casing for a watch module includes an integrally molded wristband. The casing also includes a metal form partially covered by integrally molding a thermoplastic material over the form and may, by design, leave sections of the underlying metal exposed. Attachment of the wristband to the wearer's wrist involves clasp portions that nest together, held by interlocking projections formed at the edges of the clasp portions.

Known fasteners, including hook and loop strips and interlocking structures, present some difficulties when adjusting the loop size of a strap. The fastening characteristics of hook and loop closures ensure that, whenever the hooked material and the looped fabric are near each other they tend to cling to one another. Premature clinging may occur requiring several attempts to adjust the loop to the desired size. The hook portions pick up undesirable debris like lint, hair, and other fibrous matter that impairs performance. Interlocking straps include molded rib structures that need aligning before interlocking the fastener components, and may be difficult to remove or may otherwise be inflexible.

It would, therefore, be desirable and advantageous to devise a durable low-cost, low-part count wristband (which can be made of a flexible polymer or polymeric material) with secure fastening, easy removal and convenient strap loop size adjustment.

SUMMARY OF THE INVENTION

A reclosable fastener includes an insert element and a retention element. The insert element has opposing surfaces, opposing side edges, and at least one end. The retention element has a central longitudinal axis, opposing surfaces, opposing side edges, at least one end. The retention element also has a plurality of discrete, spaced projections extending generally orthogonally from at least one side edge of one of the opposing surfaces. At least one of the projections has a free end that includes a hook portion extending generally orthogonally from the projection toward the central longitudinal axis. The width of the insert element can be equal to or less than the width of the retention element The fastener operates in a first condition and a second condition. In the first condition the fastener is open and the insert element is disengaged from the retention element. In the second condition the fastener is closed and the insert element engages the retention element such that the hook portion of the retention element faces the adjacent surface of the insert element.

In moving from the first condition to the second condition the insert element engages the retention element by overlaying onto the retention element and being pressed into place. In moving from the second condition to the first condition the insert element disengages from the retention element by peeling from the retention element.

The fastener has a shear holding function that is independent of the force required to engage and disengage the insert element and the retention element to move from the first condition to the second condition and from the second condition to the first condition.

Optionally, in the second condition the opposing side edges of the insert element can contact the spaced projections of the retention element.

Optionally, the insert element includes a plurality of discrete, spaced projections extending from at least one opposing side edge in the plane of at least one of the opposing surfaces.

The reclosable fastener can be made of only a single functional material that permits the projections on the retention element to flex during engaging and disengaging. The single functional material can be an element, a compound, a mixture, or a combination. Also, the reclosable fastener can be made integrally as one piece or as two separate pieces.

DETAILED DESCRIPTION

Figure 1:
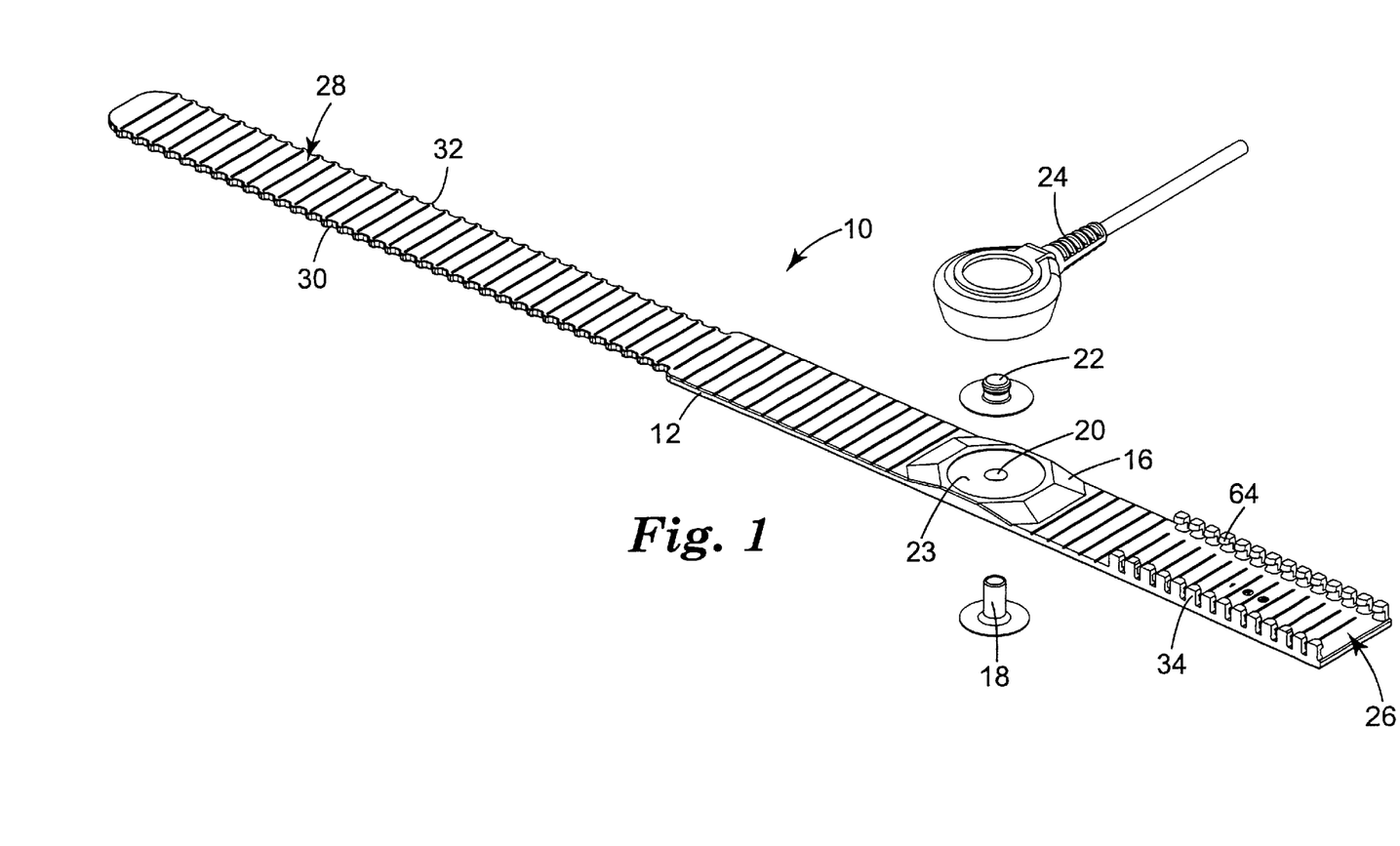
FIG. 1 is an exploded perspective view of one embodiment of the fastener of the present invention.
Figure 2:
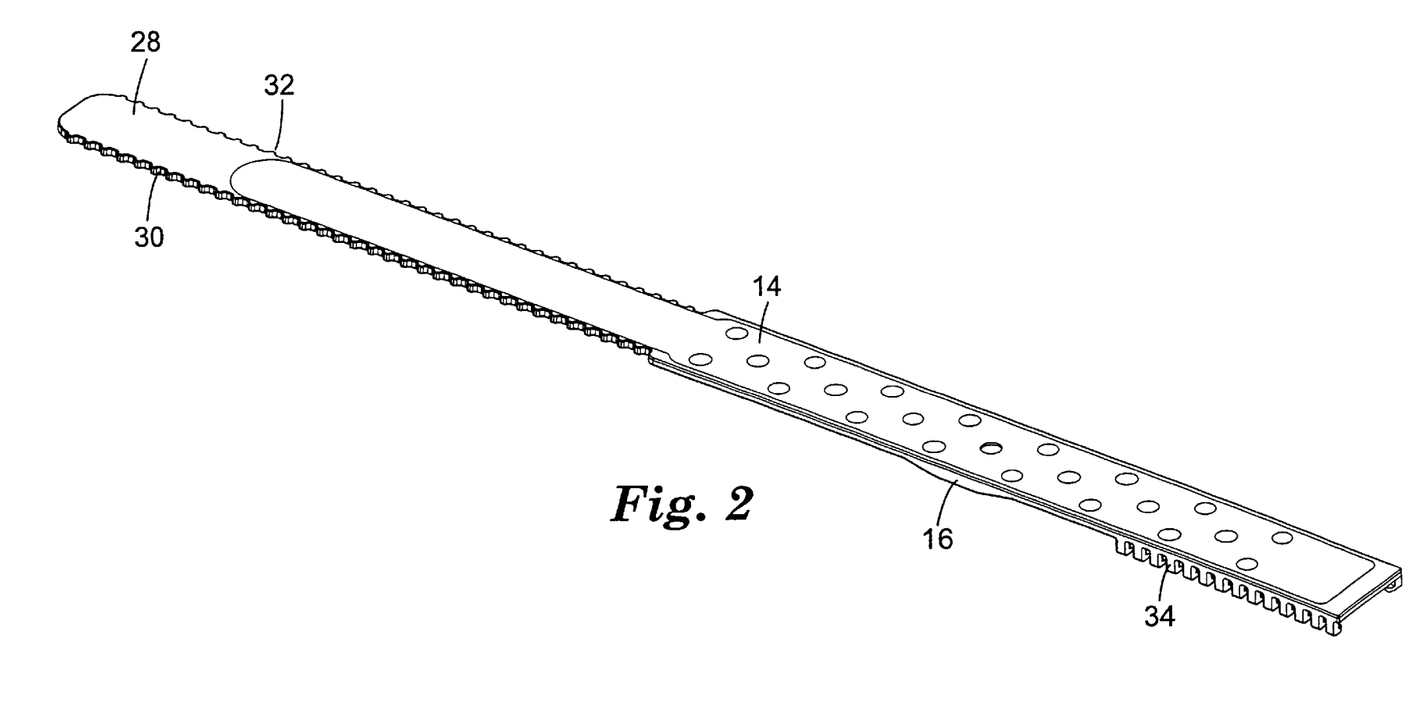
FIG. 2 is a perspective view of the inner surface of the fastener of FIG. 1.

FIGS. 1 and 2 show one embodiment of the static control wristband 10 of the present invention. The wristband 10 includes a strap 12 formed of an electrically insulative, flexible, polymeric material, with an integrally molded, electrically conductive layer 14 (FIG. 2 only). The wristband and its fastener components can be formed by molding, extrusion such as by profile extrusion, casting and curing, vacuum forming, or other methods. The conductive layer 14 can be permanently attached to the strap 12 by means of, for example, overmolding, co-molding or insert molding. The strap 12 can be made from a variety of flexible, moldable thermoplastic polymers including polyolefins, polyurethanes, and vinyl-containing thermoplastics having required resiliency in terms of tensile strength, elongation, impact resistance and related physical properties. The wristband 10 can be constructed of Hytrel® durable thermoplastic elastomer (polybutylene terephthalate/polyether glycol) available from E.I. duPont de Nemours, Wilmington, Del. The conductive layer 14 can, for example, be a metallic material or a polymeric material which has been loaded with a conductive filler to render it at least partially conductive (surface resistivity of less than $1\times10^6$ Ω/sq), so that it can dissipate electrostatic buildup on the wearer of the wristband 10. A suitable material can be a thermoplastic polymer, preferably Hytrel® durable thermoplastic elastomer, loaded with a conductive carbon powder, between 5–40% weight) depending on particle quality and size.

The conductive layer 14 is placed along the strap 12 and extends over a thickened portion 16. An electrically conductive eyelet 18 passes through a hole in the conductive layer 14 and a hole 20 in the thickened portion 16 of the strap 12, and is affixed to a male snap part 22 which interconnects the wristband 10 to a grounding tether 24. Different size snaps or studs (for example, 4 mm, 5 mm, 7 mm, or 10 mm) can be attached to the strap 12. A depression 23 in the thickened portion 16 of the strap 12 can receive the snap or stud.

To allow adjustment of the wristband, a two-part, resilient, separable reclosable fastener can be part of the strap 12. It can be formed by molding in a single molding operation, or by other methods. One part of the fastener is formed on one end of the strap 12 while the second part of the fastener is formed on the opposite end of the strap 12. The fastener includes a retention element 26 and an insert element 28. The insert element can be twice as long as the retention element and can have a series of alternating indentations 30 and pointed projections 32 along opposing side edges causing the width of the insert element 28 to vary periodically along its length. Upon closing the fastener the indentations 30 mesh with spaced 34 along the edges of the retention element 26. The projections 34 define a groove disposed longitudinally above the insulated surface of the strap 12.

Figure 3:
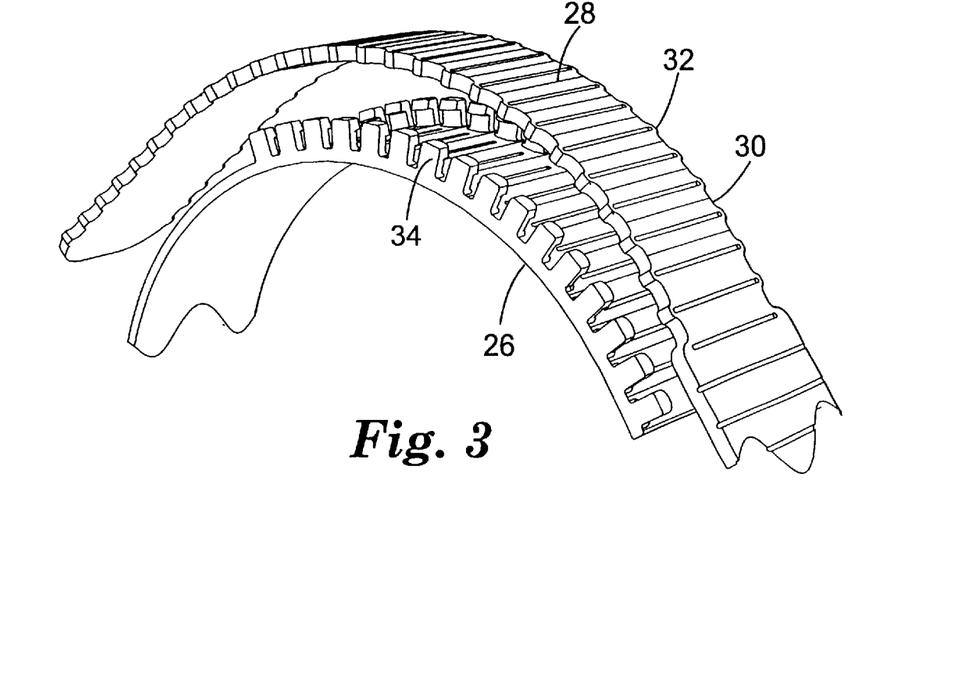
FIG. 3 is a perspective view of the fastener of FIG. 1 in a first condition.
Figure 4:
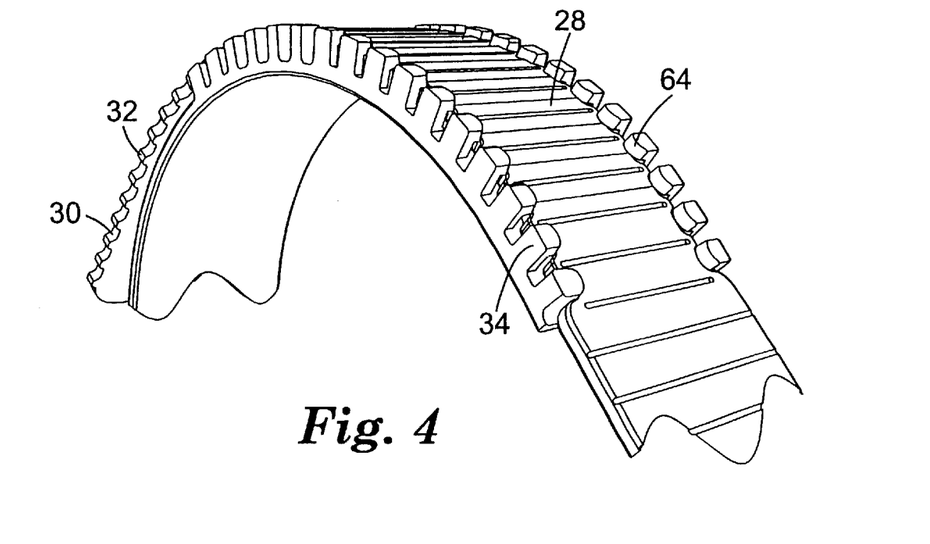
FIG. 4 is a perspective view of the fastener of FIG. 3 in a second condition.

FIG. 3 shows the retention element 26 positioned below the insert element 28 before applying pressure from above, below, or both to this combination to interlock the two elements and intermesh the insert element inside the retention element, as shown in FIG. 4, so that the projections 34 align with the indentations 30. Hooked tips or hook portions 64 can be on the projections 34 of the retention element 26 to overlap and capture the sides of the insert element 28 and insure more secure retention.

During interlocking of the retention and insert elements, the projections 34, along the sides of the retention element 26, flex sufficiently to allow entry of the insert element 28 so that it intermeshes with the retention element 26. The relative positioning of the insert and retention elements controls the size adjustment of the wristband.

There are several advantages to this design. In addition to providing all of the basic characteristics of a grounding wrist strap, the wristband 10 is so comfortably adjustable that one size fits all, with positive skin contact. It has a low manufacturing cost, particularly when as few as four parts are used (strap 12, conductive layer 14, eyelet 18, and snap 22). A pigment can be added during manufacturing to easily select appropriate colors. Manufacture of the wristband 10 is otherwise relatively facile using overmolding to fabricate the integrated strap. In overmolding, a first material, sized and shaped to desired dimensions, can be integrally combined with a second material by injection of the second material, usually in liquid form, into a suitable die to surround the first material, held in a predetermined position, within the die. The overmolding process occurs using well-known injection molding techniques. In this case, the electrically conductive layer 14, die-cut from a sheet of suitable conductive material, is positioned in a preformed depression and can be held by vacuum surfaces to hold the component inside one surface of the mold cavity that is designed for injection molding to combine the parts into a wristband. Thereafter, the injection mold cavities are closed. A thermoplastic resin is injected in a melted state into a cavity. As the cavity is filled the flexible polymer cools, forming the strap 12 with its exposed conductive surface and its integrally molded insert and retention elements. Then the mold cools for ejection of the part from the mold.

After removal from the mold, the eyelet 18, passed through the hole 20, can secure the male snap 22 to the thickened portion 16 of the wristband. At the same time, the eyelet 18 establishes electrical contact between the snap 22 and the conductive layer 14 that will contact the wearer's skin during use of the wristband with a grounding cord to remove static charge.

The invention is more than a static control wristband. The fastener of the invention can be used for various diverse purposes. The reclosable fastener itself is novel and improves upon known fasteners. A first embodiment of this fastener is shown in FIGS. 1 and 2. Other embodiments are shown in FIGS. 5–9. Discussing the fastener features in detail, as shown in FIGS. 5–9, the reclosable fastener, like that used on the wristband 10 of FIGS. 1–4, includes an insert element 28 and a retention element 26. These elements can be separate (FIG. 11) or they can be connected by some form of coupling (FIGS. 1–9), in addition to the connection when they are engaged. They can be made integrally as one piece or of two separate pieces. The insert element 28 has opposing surfaces 40, 42, opposing side edges 44, 46, and at least one end 48. The retention element 26 has a central longitudinal axis 50, opposing surfaces 52, 54, opposing side edges 56, 58, and at least one end 60. If the insert element 28 and the retention element 26 are separate pieces, then they each have two free ends.

The retention element 26 has a plurality of discrete, spaced projections 34 extending generally orthogonally from at least one side edge of one of the opposing surfaces. As shown, a plurality of projections 34 extend from both side edges 56, 58. Projections 34 on opposing side edges 56, 58 can be aligned, staggered, or in any other configuration. Also as shown, each projection 34 has a free end 62 that terminates in a hook portion 64 extending generally orthogonally from the projection and generally toward the central longitudinal axis 50 of the retention element 26. The hook portion 64 need not point directly to the longitudinal axis 50; they can point at an angle.

The insert element 28 can have smooth side edges 44, 46 and the fastener will perform well. With smooth sides, the width of the insert element 28 can be equal to or less than the width of the retention element 26. As shown, a plurality of discrete, spaced projections 32 extend from both opposing side edges 44, 46 in the plane of one of the opposing surfaces 40. These projections 32 are located to correspond to spaces 66 between projections on the retention element. The large number of respective projections 32, 34 on both the insert element 28 and the retention element 26 means that the fastener can be closed in a large number of positions to finely vary the strength of the closure and the overlap distance of the two elements. In this configuration (with projections 32 on the insert element 28), the width of the insert element 28 can be equal to, less than, or even greater than the width of the retention element 26. In known fasteners the width must be less than that of the retention element.

The fastener operates in first and second conditions. In the first condition the fastener is open and the insert element 28 is disengaged from the retention element 26. In the second condition the fastener is closed and the insert element 28 engages the retention element 26. In this second, closed condition, the hook portion 64 of the retention element 26 faces the adjacent surface of the insert element. Optionally, the opposing side edges 44, 46 of the insert element 28 can also contact the spaced projections 34 of the retention element 26.

When moving from the first condition to the second condition the insert element 28 engages the retention element 26 by overlaying onto the retention element and being pressed into place. Closing is not effected by sliding the two elements in shear. In moving from the second condition to the first condition the insert element 28 disengages from the retention element 26 by peeling from the retention element. Shear can be used to open the fastener, but it is much easier to open by peeling.

The term peel is used to mean to strip away or to pull off the insert element from the retention element in a direction generally orthogonal to the plane of the retention element. This direction is orthogonal to a shearing direction. The term overlay is used to mean to press into place; this is a counterpart to peel and also is in a direction orthogonal to a shearing direction. Shear means opposite and parallel sliding motion in the planes of the insert and retention elements when the fastener is in the closed, second condition. The peel force to open the fastener is related to the length of the projections on the retention element. The shear force that the fastener resists is related to the length of the projections on the insert element. Furthermore, the properties of the material used for the fastener, particularly the hardness of the material, dictates, at least in part, the peel and shear strength of the fastener. During use in the second condition the fastener has a shear holding capability that resists shear forces of at least 1.5 times the force required to disengage by peeling.

Because the insert element 28 and retention element 26 of the fastener engage and disengage using peel, the fastener has a shear holding function that is independent of the force required to engage (overlay) and disengage (peel) the insert element and the retention element to move from the first condition to the second condition and from the second condition to the first condition.

The reclosable fastener can be made of only a single functional material that permits the projections on the retention element to flex during engaging and disengaging. This single functional material can be an element, a compound, or a mixture, or a combination of these. Alternatively, the reclosable fastener can be made of multiple materials, such as with the projections being formed of a different material from the rest of the fastener.

Figure 8:
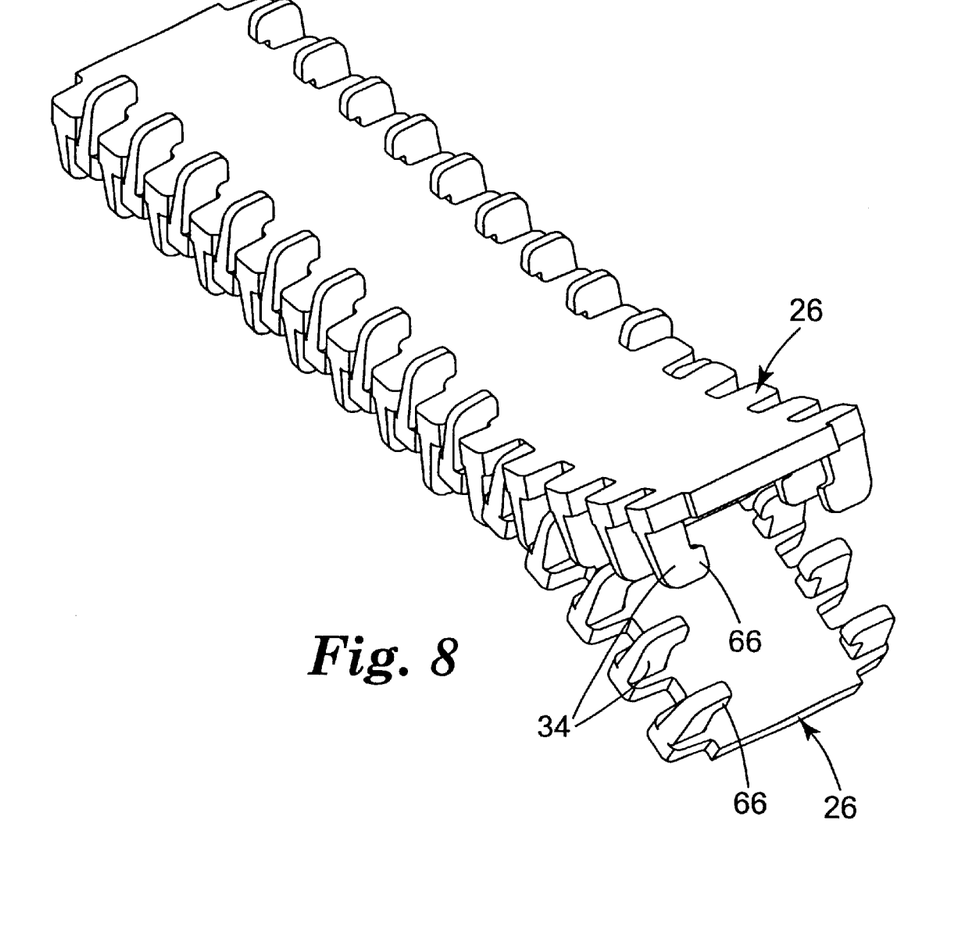
FIG. 8 is a perspective view of another embodiment of the fastener of the present invention in one second condition.
Figure 9:
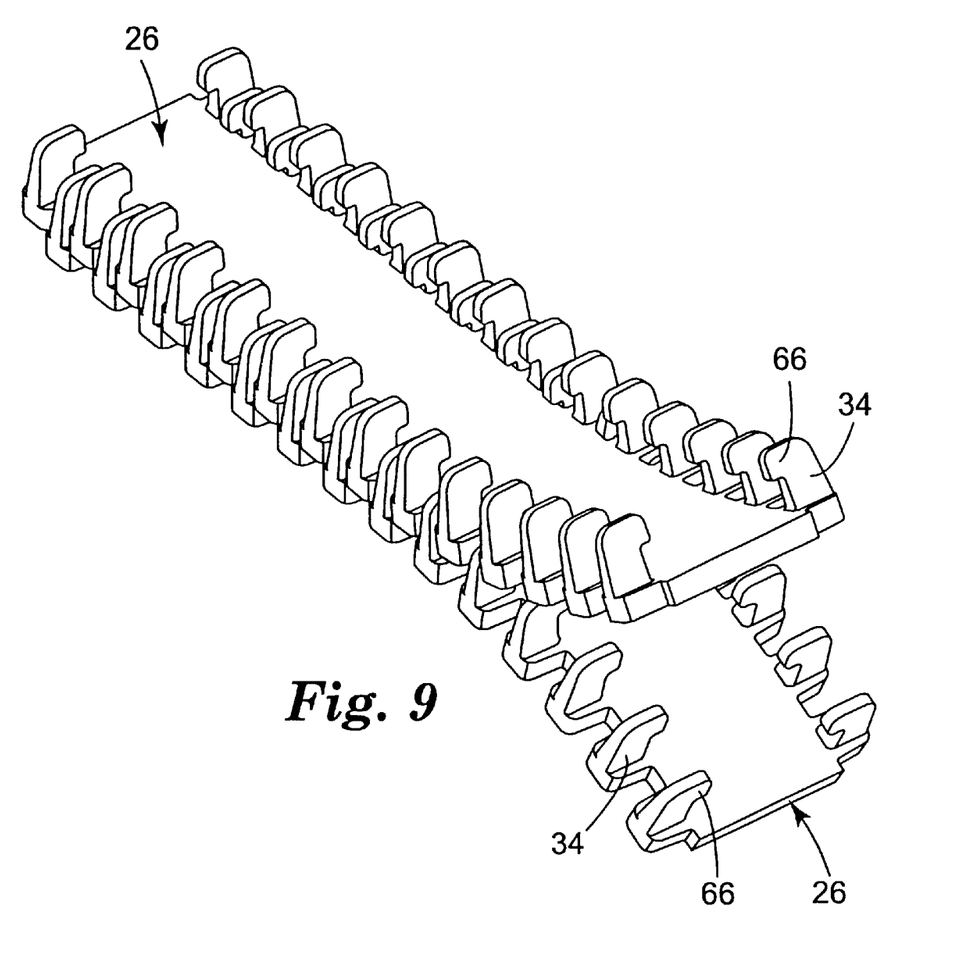
FIG. 9 is a perspective view of the fastener of FIG. 8 in another second condition.

FIG. 8 and 9 show an embodiment of this reclosable fastener in which a single element is used. This element has a similar structure to that of the retention element 26 of the other embodiments. This element can mate with itself both front to front, as shown in FIG. 8, or front to back, as shown in FIG. 9. Stronger shear hold occurs in the front to front engagement.

Figure 12:
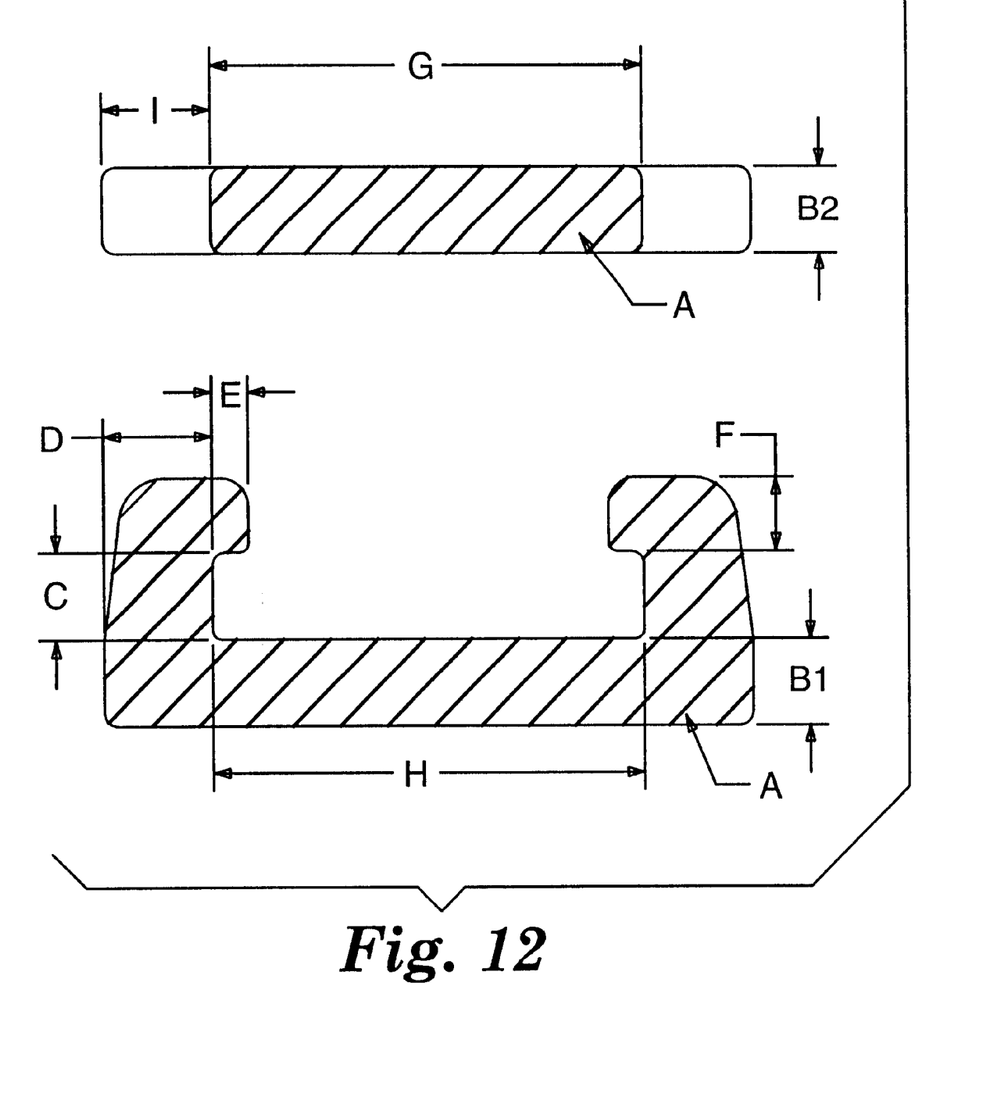
FIG. 12 is a cross-sectional view of the fastener of the invention.

The fastener has various parameters that determine how it performs such tasks as closing, holding, and opening. These parameters can be varied to change the performance of the fastener. FIG. 12 illustrates the dimensions that effect performance of the fastener. These parameters include the material hardness (A), the retention element thickness (B1), the insert element thickness (B2), the retention element projection height (C), the retention element projection thickness (D), the hook overhang (E), the hook thickness (F), the width of the insertion element from projection to projection (inside width) (G), the width of the retention element from projection to projection (inside width) (H), the insert element projection length (I), the number of teeth per unit length (J), width interconnect space (H–G) (H minus G), the thickness interconnect space (C–B) (C minus B), the projection interlock (2I+G–H) (2 times I plus G plus H), and the angle of the hook. For example, increasing the holding strength enables the fastener to be used with heavier objects or in environments with large forces placed on the fastener.

The following examples illustrate the usefulness of these fasteners. The fasteners in these examples were tested for shear and peel performance using ASTM D5169 Test Method for Shear using a 2.54 cm (1 in) overlap and ASTM D5170 for Peel. The table below summarizes the results.

| Example | Shear kN/m (lb$_f$in) | Peel kN (lb$_f$) | Shear/Peel Ratio |
| --- | --- | --- | --- |
| 1 | 0.445 (2.6) | 0.0013 (0.29) | 9.0 |
| 2 | 0.084 (0.48) | 0.0002 (0.04) | 12 |
| 3 | 0.453 (3.1) | 0.0016 (0.37) | 8.4 |
| 4 | 1.348 (7.7) | 0.0016 (0.35) | 22 |
| 5 | 3.835 (21.9) | 0.0038 (0.86) | 25.5 |

It is clear from the test data and the examples that by changing materials and fastener element dimensions, a wide variety of performance characteristics can be achieved. All percentages listed are percentages by weight.

EXAMPLE 1

The static control wrist strap of FIGS. 1–4 illustrates this construction. The fastener is an integrated construction incorporating both the insert element and the retention elements. This band was molded using a blend of Hytrel® polymers 50% #3078, 46% #4069 & 4% color concentrate. The dimensions for the fastener are:

| | |
| --- | --- |
| Material Hardness (A) | 86 shore A |
| Strap Thickness (B1 & B2) | 1.4 mm (0.055 in) |
| Retention Element Projection Height (C) | 1.5 mm (0.059 in) |
| Projection Thickness (D) | 1.2 mm (0.047 in) |
| Projection Overhand (E) | 0.59 mm (0.023 in) |
| Hook Thickness (F) | 0.80 mm (0.034 in) |
| Insert Element inside Width (G) | 12.6 mm (0.496 in) |
| Retention Element Inside Width (H) | 12.95 mm (0.510 in) |
| Insert Element Projection Length (I) | 1.27 mm (0.050 in) |
| Number of Retention Element Rows (J) | 0.33 mm (8.33 in) |
| Width Interconnect Space (H – G) | 0.35 mm (0.014 in) |
| Thickness Interconnect Space (C – B2) | 0.1 mm (0.004 in) |
| Projection Interlock (2I + G – H) | 2.18 mm (0.086 in) |

This construction gave good performance in a wristband application.

EXAMPLE 2

This fastener was produced with the same fastener dimensions as Example 1, except that the fastener was made with an SEBS copolymer #1601 from QST Inc. St. Albans, Vt. The material hardness (A) is 55 shore A. This material is very soft and elastic and reduces the peel and shear values.

EXAMPLE 3

This fastener was produced with the same fastener dimensions as Example 1, except that the fastener was made with 96% duPont/Dow Engage® #8403 polymer with 4% color concentrate. FIGS. 1–4 illustrates this construction. The material hardness (A) is 95 shore A.

EXAMPLE 4

This fastener was molded using 96% Hytrel® #G3578W and 4% color concentrate. The dimensions for the fastener are:

| | |
| --- | --- |
| Material Hardness (A) | 85 shore A |
| Strap Thickness (B1 & B2) | 1.5 mm (0.059 in) |
| Latch Base height (C) | 2.06 mm (0.081 in) |
| Projection Thickness (D) | 2.64 mm (0.104 in) |
| Projection Overhand (E) | 0.86 mm (0.034 in) |
| Hook Thickness (F) | 1.70 mm (0.067 in) |
| Insert Element Inside Width (G) | 10.16 mm (0.400 in) |
| Retention Element Inside Width (H) | 10.31 mm (0.406 in) |
| Insert Projection Length (I) | 2.64 mm (0.104 in) |
| Number of Retention Element Rows (J) | 0.23 mm (5.9 in) |
| Width Interconnect Space (H – G) | 0.15 mm (0.006 in) |
| Thickness Interconnect Space (C – B2) | 0.56 mm (0.022 in) |
| Projection Interlock (2I + G – H) | 5.13 mm (0.202 in) |

Figure 5:
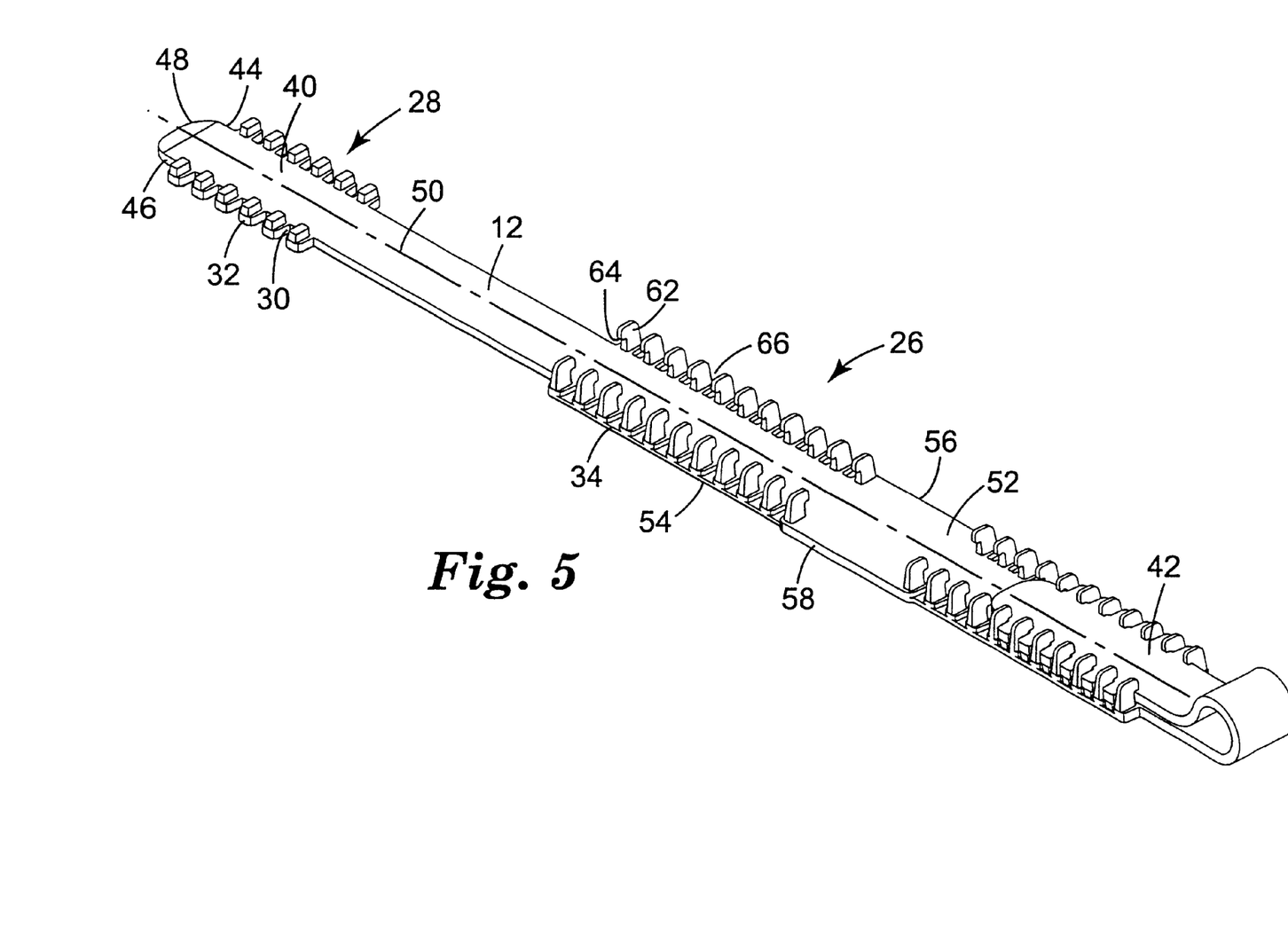
FIG. 5 is a plan view of another embodiment of the fastener of the invention with multiple closures.

This fastener is shown in FIG. 5. The insert element of one end loops 180° into the retention element. The projections 32 on the insert element 28 engage into the spaces 66 on the retention element 26. This increases the insert element thickness to enhance the peel disengagement force.

EXAMPLE 5

Figures 6, 7:
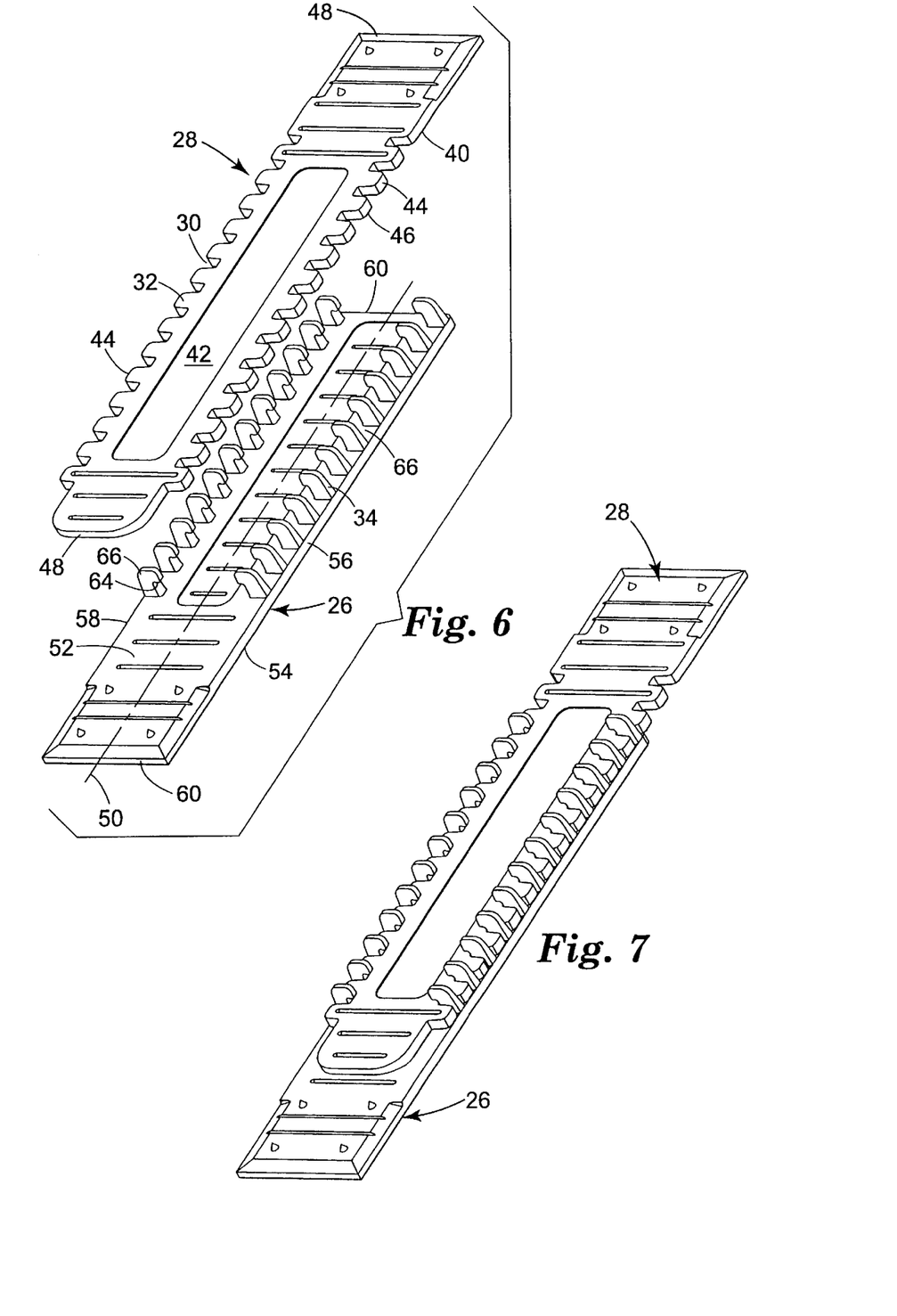
FIG. 6 is a perspective view of another embodiment of the fastener of FIG. 5 in a first condition.
FIG. 7 is a perspective view the fastener of FIG. 5 in a second condition.

This example used the fastener configuration of FIGS. 6 and 7. This band was molded using 96% Hytrel® #4556 and 4% color concentrate. The dimensions for the fastener are:

| | |
| --- | --- |
| Material Hardness (A) | 96 shore A |
| Strap Thickness (B1 & B2) | 1.5 mm (0.059 in) |
| Latch Base height (C) | 2.06 mm (0.081 in) |
| Projection Thickness (D) | 2.64 mm (0.104 in) |
| Projection Overhand (E) | 0.86 mm (0.034 in) |
| Hook Thickness (F) | 1.70 mm (0.067 in) |
| Insert Element Inside Width (G) | 13.77 mm (0.542 in) |
| Retention Element Inside Width (H) | 13.92 mm (0.548 in) |
| Insert Projection Length (I) | 2.64 mm (0.104 in) |
| Number of Retention Element Rows (J) | 0.23 mm (5.9 in) |
| Width Interconnect Space (H – G) | 0.15 mm (0.006 in) |
| Thickness Interconnect Space (C – B2) | 0.56 mm (0.022 in) |
| Projection Interlock (2I + G – H) | 5.13 mm (0.202 in) |

Figure 11:
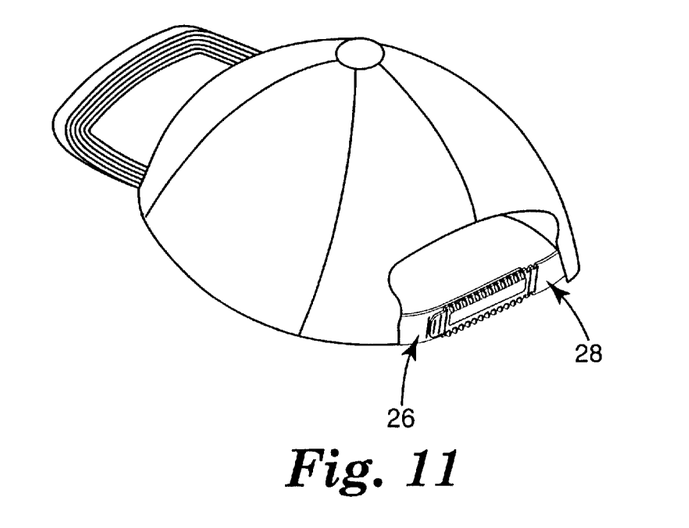
FIG. 11 is a perspective view of a baseball cap with the fastener of the present invention used for cap size adjustment.

This fastener was used as a hat fastener, as shown in FIG. 11. The fasteners were hemmed inside the fabric rim at the back of the hat.

The fastener can be used as a wristband which can be applied to a user's wrist in a simple, one-handed procedure. For discussion here, the wristband 10 of FIGS. 1–4 will be used as an example. For application to the wearer's right wrist, the wristband 10 is held between thumb and forefinger of the left hand, the thumb being in contact with the snap 22. Then the right arm is extended forward, palm down. The wristband 10 is laid on top of the wrist, with the retention element 26 behind the wrist bone, so that the length of the band will wrap around the wrist. In this position, the band is held against the right wrist by exerting pressure against the snap 22 with the thumb of the left hand. The wristband is then held between the top portion of the right wrist and the thumb of the left hand. It is possible to hold this position, by thumb pressure on the snap 22, while reaching below the right wrist with the fingers of the left hand to grasp the retention element 26 and draw it under and around the right wrist. This allows for an adjustment to a position where the left thumb holds the band 10 by the snap 22, above the top of the wrist, and the left middle finger holds the retention element 26 against the underside of the right wrist. While holding the position of the retention element 26, the thumb of the left hand is moved along the strap 12, away from the snap 22, towards the insert element 28, taking care to keep the wristband taut against the right wrist. During this movement, the left thumb travels down the inside of the right wrist and begins to loop the wristband around the right wrist. Just before reaching the middle of the underside of the right wrist, the insert element 28 begins to interlock with the retention element 28. Thumb pressure is applied until the insert element lies inside the retention element. This one-handed procedure usually results in a snug fit of the wrist strap around the wearer's wrist.

Figure 10:
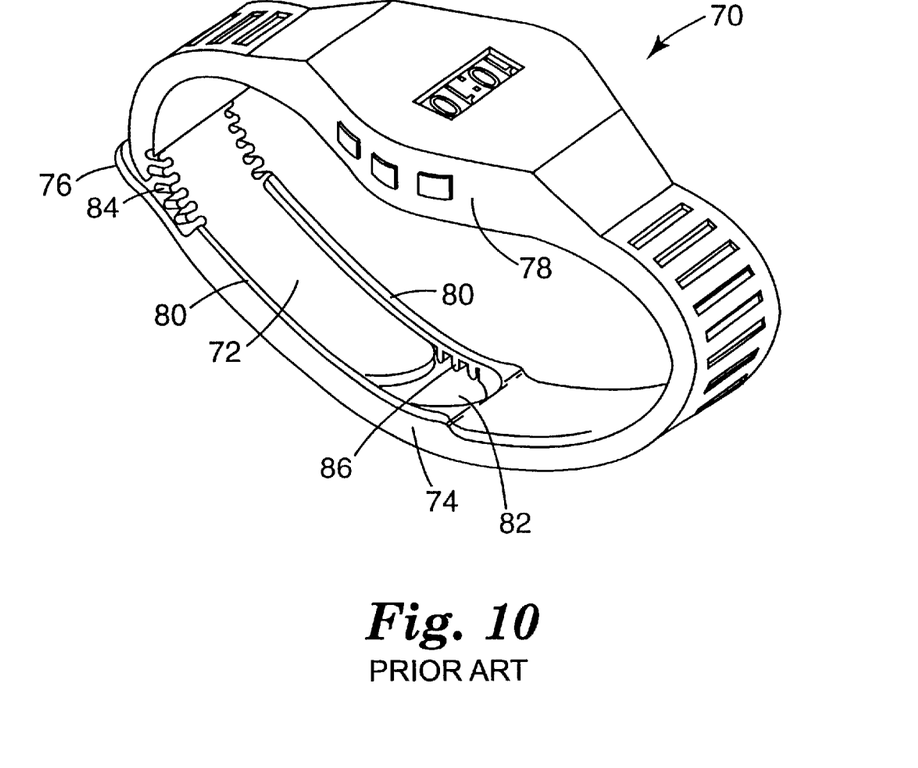
FIG. 10 is a perspective view of a known wristband.

The ease of application of the wristband of the current invention provides marked contrast to the known wristband of FIG. 10, which is disclosed in U.S. Pat. No. 4,178,751. At least two aspects of the known band show deficiencies compared to the current invention. First, the known band 70 requires multiple processes to attach the male 72 and female 74 clasp portions on opposite ends, followed by overmolding, using injection molding techniques. Thereafter, attempts to apply the wristband with one hand, as described previously, usually result in failure. Even where it is possible to unite the male 72 and female 74 clasp portions of the wristband, there is poor contact between the user's wrist and the inner surface of the wristband. It is noticeable that the orientation of male 72 and female 74 portions, as shown in FIG. 10, causes the open side of the female clasp portion to face the surface of the wrist, preventing entry by an overlapping male portion. Reversal of the positions of the clasp portions, relative to the wrist surface, requires the female portion to spread around the male portion. The female portion does not open readily; the female portion is disclosed as rigid, with the male portion bowing to be able to insert into the female portion. Action to unite the male and female clasp portions meets resistance because of the stiffness of the wristband. In an apparent attempt to facilitate clasp closure, a tab 76 is formed on the female portion 74. The tab 72 may be held with one hand while applying pressure on the male clasp portion to urge it to move into the female clasp. Use of such a tab requires two hands. Considering difficulties associated with applying the wristband, and the increased part count and processes required to fabricate the known band, the current invention provides greater convenience and ease of application.

U.S. Pat. No. 4,178,751 provides dimensions for the wristwatch concept.

There are several differences between the known band 70 and the current invention providing advantages for the current invention. A preliminary observation (see FIG. 10 of this specification) reveals that the known band 70 includes separate parts for the male clasp portion 72, the wristband section 78 and the female clasp portion 74. Each part is made from a different material and, in addition, the wristband section has an internal stiffening, metal band appearing to provide reinforcement to the wristband section 78. The known band requires several separate processes for its manufacture, including production of the metal band, the male clasp portion, the female clasp portion and finally the overmolding process to unite these parts together. Additionally, it is difficult to engage the '751 strap. This known strap requires approximately the same force to engage it as to disengage it because both engagement and disengagement require shear motions.

While reproduction of the known band could lead to significant expenditure to reproduce the multiple processes, it is possible to obtain some indication of performance characteristics of the known band by molding a one-piece unit using a single material, similar in physical properties to the material used for the current invention. Formation of this modified known band required the well-known combination of stereo-lithography and vacuum casting processes. The first process, of stereo-lithography produced a solid model of the known watch strap. This model was surrounded by a commonly used, moisture cure silicone casting material to produce a silicone mold for casting reproductions of the known watch band using a variety of curable compositions. Suitable curable compositions have physical properties, after curing, closely paralleling those of the injection molding material used for the current invention.

Known parts, produced by stereo-lithography and vacuum casting, proved to be inferior in flexibility and design when compared to the current invention. For example, the use of similar durometer materials did not compensate for the fact that the known watch band requires a thicker band cross-section than the current invention resulting in a stiffer product. This condition exists even without internal reinforcement of the strap by a metal band. Such a metal band would further increase the stiffness of the known watch strap, causing a problem with wrapping the strap around a wearer's wrist. Evidence of deficiencies of design arises with any attempt to unite the known male 72 and female 74 clasp portions in similar fashion to the current invention. Upon inspection it is clear that the known female clasp portion 74 faces the opposite direction to that which facilitates entry of the male portion 72 into the female portion. Also, the edges 80 defining the slot 82 of the female clasp portion 74, represent barriers to the intermeshing of teeth 84, on the male portion 72 with channels 86 in the female clasp portion. Thus, it is not possible to simply align the teeth 84 of the male portion 72 over the receiving channels 86 of the female portion 74 and cause the two parts to interlock simply by applying pressure to the male clasp portion. In fact the '751 patent does not teach unifying the watch strap closure by this overlap method, but advises the use of a tab 76 to stabilize the female portion 74 while pushing the male portion into the closure slot 82. Unfortunately, this requires one hand to hold the tab and another hand to push the insert element into place, usually requiring assistance from another person.

The fastener of the present invention can be used as a fastener in many areas. For example, it can be used with clothing. Clothing includes items such as shirts and coats, shoes, caps and visors with adjustable straps, trouser belts, watch straps, ornamental items such as bracelets, rings, headbands or armbands, heel straps, including those for grounding static charge, and the like.

FIG. 11 shows a fastener of the invention used with a baseball cap to facilitate size adjustment to the wearer's head. Insert element 28 readily mates with retention element 26 by application of hand or finger pressure to the insert element placed in suitable alignment over the retention element. One hand may be used to fasten the fastener.

In another use, the invention provides a tie-down, tether, or binder using multiple closures. Referring back to FIGS. 5, 6, and 7, the fastener includes a strap 12 with insert elements 28 at each end. Each insert element 28 has a corresponding retention element 26 positioned closer to the center of the strap 12. In this configuration, the insert element 28 will form a loop when folded towards and united with the retention element 26. The insert element, passed through, for example, a suitably sized eyelet, will secure the eyelet to the strap, once the loop is formed. Following this principle, the multi-closure fastener acts as a link between multiple eyelets. Attachment of multiple eyelets, or slots or holes, to a single object allows use of the tie-down as, for example, a lifting handle, which facilitates maneuvering of objects such as large packages. Alternatively, the tie-down could provide temporary repair for a broken luggage handle. In another application the multi-closure fastener provides a convenient way to attach, for example, a dispenser box of swabs or wipes or similar articles to someone needing the articles as part of routine procedures. The fastener, attached to at least two points on the dispenser, provides a flexible tether, when suitably sized, to hold the dispenser to a person's hand or wrist. Use of the tether places the contents of the dispenser readily available for use, but leaves hands free for other purposes.

In other situations, an object may be too large for grasping with one hand. A multi-closure fastener of the invention attached to suitable loops or slots on such an object will allow the use of one hand to control the object in the palm of the hand with the tether gripping the back of the user's hand.

A fastener of the invention can also be used as a replacement for laces, such as for shoes. In a typical situation the retention element, attached to one side of a shoe upper, receives the insert element attached to the other side of the shoe upper to provide comfortable attachment of the shoe to a foot. The fastener is so easy to apply that a child quickly learns to form the fastener by finger pressure, on the insert element overlying, and aligned with, the retention element.

Various modifications of the invention can be made. For example, the insert element can be formed with hollow portions which define the indentations in an embodiment that does not otherwise have projections (the locations between the hollow portions could function as projections and could be called projections.

What is claimed is:

1. A reclosable fastener comprising:

an insert element having opposing surfaces, opposing side edges, and at least one end, wherein the insert element comprises a plurality of discrete, spaced projections extending orthogonally from at least one opposing side edge in the plane of at least one of the opposing surfaces; and a retention element having a central longitudinal axis, opposing surfaces, opposing side edges, at least one end, and a plurality of discrete, spaced projections extending generally orthogonally from at least one side edge of one of the opposing surfaces, wherein at least one of the projections has a free end that comprises a hook portion extending generally orthogonally from the projection and generally toward the central longitudinal axis; and wherein the fastener operates in first and second conditions, wherein in the first condition the fastener is open and the insert element is disengaged from the retention element, and in the second condition the fastener is closed and the insert element engages the retention element such that the hook portion of the retention element faces the adjacent surface of the insert element, and the insert element spaced projections engage the retention element spaced projections.

2. The reclosable fastener of claim 1 wherein in moving from the first condition to the second condition the insert element engages the retention element by overlaying onto the retention element and being pressed into place, in moving from the second condition to the first condition the insert element disengages from the retention element by peeling from the retention element, and during use in the second condition the fastener has a shear holding capability that resists shear forces of at least 1.5 times the force required to disengage by peeling.

3. The reclosable fastener of claim 1 wherein the fastener has a shear holding function that is independent of the force required to engage and disengage the insert element and the retention element to move from the first condition to the second condition and from the second condition to the first condition.

4. The reclosable fastener of claim 1 wherein in the second condition the opposing side edges of the insert element contact the spaced projections of the retention element.

5. The reclosable fastener of claim 1 wherein the width of the insert element is one of equal to, less than, and greater than the width of the retention element.

6. The reclosable fastener of claim 1 which is made of only a single functional material that permits the projections on the retention element to flex during engaging and disengaging, wherein the single functional material can be at least one of an element, a compound, and a mixture.

7. The reclosable fastener of claim 6 which is made one of integrally as one piece and of two separate pieces.

8. The reclosable fastener of claim 1 having parameters of material hardness, insert element thickness, retention element thickness, retention element projection height, retention element projection thicknesses, hook overhang, hook thickness, width of the insertion element from projection to projection, width of the retention element from projection to projection, length of the insert element projections, angle of the hook, the number of teeth per unit length, the width interconnect space, the thickness interconnect space, the projection interlock, and the angle of the hook, wherein these parameters are selected in combination with each other to control the performance of the fastener.

* * * * *

UNITED STATES PATENT AND TRADEMARK OFFICE
CERTIFICATE OF CORRECTION

PATENT NO.   : 6,256,847 B1
DATED        : July 10, 2001
INVENTOR(S)  : Norman G. Manley and Brian M. Cox Page 1 of 1

It is certified that error appears in the above-identified patent and that said Letters Patent is hereby corrected as shown below:

<u>Column 4,</u>
Line 5, "weight)" should read -- (weight) --

<u>Column 7,</u>
Line 49, "0.33 mm (8.33 in)" should read -- 0.33/mm (8.33/in) --

<u>Column 8,</u>
Line 21, "0.23 mm (5.9 in)" should read -- 0.23/mm (5.9/in) --
Line 44, "0.23 mm (5.9 in)" should read -- 0.23/ mm (5.9/in) --

<u>Column 11,</u>
Line 34, "indentations in an" should read -- indentations 30 in an --

Signed and Sealed this

Twelfth Day of March, 2002

Attest:

Attesting Officer

JAMES E. ROGAN
Director of the United States Patent and Trademark Office